US012122993B2

(12) United States Patent
Vowinkel et al.

(10) Patent No.: US 12,122,993 B2
(45) Date of Patent: Oct. 22, 2024

(54) BIOGAS DIGESTER TANK HEATING METHOD AND SYSTEM, AND MODULAR HEATING RACK FOR THE SAME

(71) Applicant: PlanET Biogas Group GmbH, Vreden (DE)

(72) Inventors: Gerrit Vowinkel, Vreden (DE); Philipp Genschick, Vreden (DE); Marco Schmitz, Vreden (DE)

(73) Assignee: PLANET BIOGAS GROUP GMBH, Vreden (DE)

( * ) Notice: Subject to any disclaimer, the term of this patent is extended or adjusted under 35 U.S.C. 154(b) by 560 days.

(21) Appl. No.: 17/186,383

(22) Filed: Feb. 26, 2021

(65) Prior Publication Data

US 2022/0275321 A1    Sep. 1, 2022

(51) Int. Cl.
*C12M 1/02*    (2006.01)
*C12M 1/107*    (2006.01)

(52) U.S. Cl.
CPC ............ *C12M 41/24* (2013.01); *C12M 21/04* (2013.01); *C12M 27/00* (2013.01)

(58) Field of Classification Search
None
See application file for complete search history.

(56) References Cited

U.S. PATENT DOCUMENTS 3,978,918 A * 9/1976 Nagatomo ............. C12M 41/24
366/147
4,670,397 A * 6/1987 Wegner .................. C12M 41/02
435/243
4,882,283 A * 11/1989 Gentry .................. F28F 9/0243
422/138
2017/0335265 A1* 11/2017 Stiller .................... C12M 27/06

FOREIGN PATENT DOCUMENTS

| CN | 202246670 | * | 5/2012 |
| CN | 209602509 | * | 11/2019 |
| DE | 19805580 | * | 9/1999 |
| DE | 202007002835 U1 | * | 7/2007 |

(Continued)

OTHER PUBLICATIONS

WIPO, International Search Report and Written Opinion for PCT/EP2022/054657, Jun. 14, 2022.

*Primary Examiner* — Holly Kipouros
*Assistant Examiner* — Nathan G Esperon
(74) *Attorney, Agent, or Firm* — Hodgson Russ LLP

(57) ABSTRACT

A biogas digester tank heating method, system and modular heating rack is provided. The method can include providing a digester tank having a base and a vertical wall surrounding the base. A plurality of heating racks can be provided, where each of the plurality of heating racks is a pre-assembled unit including a plurality of parallel pipes and a stand configured to secure the plurality of parallel pipes to the base of the biogas digester tank. The plurality of heating racks can be secured to the base, adjacent to the vertical wall. Each of the plurality of heating racks can be connected to a heating manifold arranged outside of the digester tank in parallel such that a heat exchange fluid is configured to independently flow from the heating manifold through the plurality of parallel pipes of each individual heating rack of the plurality of heating racks.

10 Claims, 7 Drawing Sheets

(56) References Cited

FOREIGN PATENT DOCUMENTS

| | | | |
|---|---|---|---|
| KR | 101025537 | * 4/2011 | |
| KR | 20180107435 | 10/2018 | |
| KR | 102019628 | 9/2019 | |
| WO | WO-2010136318 A1 * | 12/2010 | ............ C12M 21/04 |
| WO | 2014004932 | 1/2014 | |
| WO | WO-2014004932 A1 * | 1/2014 | ............ C12M 21/04 |

* cited by examiner

BIOGAS DIGESTER TANK HEATING METHOD AND SYSTEM, AND MODULAR HEATING RACK FOR THE SAME

FIELD OF THE DISCLOSURE

This disclosure relates to heating systems and methods, and more particularly, to a biogas digester tank heating method and system, and a modular heating rack for the same.

BACKGROUND OF THE DISCLOSURE

In a biogas generation system, microbiological methanation occurs in the digester tank. To achieve optimum biogas yield, constant environmental conditions are needed. In particular, the temperature inside the digester tank must be controlled within acceptable levels. Temperature control can be achieved using a heating system installed with the digester tank system. However, prior heating systems present certain problems.

A first type of heating system is mounted to the inner wall of the digester tank. For example, pre-bent stainless steel pipes are mounted on the wall around the circumference of the digester tank to form a single heat exchange flow path. However, this type of heating system is difficult and time consuming to install due to the need to custom fit, mount, and secure ends of individual pipes on the digester tank wall. In addition, mounting hardware used to secure such piping can adversely affect the structural integrity of the digester tank wall. This is particularly true as such heating systems are typically installed in digester tanks whose walls are made of concrete.

A second type of heating system is mounted to a ground slab inside the digester tank. For instance, pre-bent stainless steel pipes are mounted on stainless steel supports fixed to the ground around the circumference of the digester tank to form a single heat exchange flow path. However, this type of heating system is also difficult and time consuming to install due to the need to custom fit and mount each pipe on supports, secure ends of each pipe together, and affix the supports to the ground. While this type of heating system can be used with a digester tank having stainless steel walls, it is more expensive than a wall-mounted heating system, and still presents the same problems.

A third type of heating system is embedded in the walls of the digester tank. For example, flexible pipes can be installed on the rebar network before concrete is poured when forming the walls of the digester tank. However, this type of heating system is susceptible to damage to the pipes when pouring the concrete. Consequently, it is very difficult to repair damage to pipes that occurred during the pouring process or when other components are mounted to the walls of the digester tank. This type of heating system is only suitable for a digester tank with concrete walls, and it is less efficient than wall-mounted or ground-mounted systems due to the lower heat transfer coefficient of concrete as compared to metals.

Prior art heating systems suffer from difficult, costly, and time consuming maintenance and repair. Due to their custom installations, repair can only be done on-site, which causes long disruptions to system operations. In addition, testing and adjustments of the heating systems can only be done on-site by specialized technicians. Consequently, the quality of heating system cannot be ensured until it is installed. Individual connections between adjacent pipes must be tested on-site before the heating system can be safely operational.

Therefore, what is needed is a heating system, as well as a digester tank system with a heating system that is easy to install and maintain, and is suitable for digester tanks of varying sizes and materials.

BRIEF SUMMARY OF THE DISCLOSURE

A biogas digester tank heating method, system and modular heating rack is provided. According to a first embodiment, a biogas digester tank heating method can include providing a digester tank having a base and a vertical wall surrounding the base. A plurality of heating racks can be provided, where each of the plurality of heating racks is a pre-assembled unit including a plurality of parallel pipes and a stand configured to secure the plurality of parallel pipes to the base of the biogas digester tank. The plurality of heating racks can be secured to the base, adjacent to the vertical wall. Each of the plurality of heating racks can be connected to a heating manifold arranged outside of the digester tank in parallel such that a heat exchange fluid is configured to independently flow from the heating manifold through the plurality of parallel pipes of each individual heating rack of the plurality of heating racks.

In one example, the plurality of heating racks can be connected to a heating manifold by connecting an inlet pipe of the plurality of parallel pipes of each heating rack to an inlet port in the digester tank. An outlet pipe of the plurality of parallel pipes of each heating rack can be connected to an outlet port in the digester tank. The inlet pipe and the outlet pipe can emanate vertically from each heating rack, and the inlet port and the outlet port are located at a height above the height of the heating rack. The plurality of parallel pipes can be substantially straight, with a curvature of less than 20 degrees.

According to certain embodiments, at least one agitator can be secured to the vertical wall and disposed between the plurality of heating racks and the vertical wall. The plurality of heating racks can be spaced at regular intervals around a center of the digester tank, and the at least one agitator may be centrally located in a space between adjacent heating racks of the plurality of heating racks.

According to another embodiment, a biogas digester tank heating system is provided. The system can include a plurality of heating racks configured to be spaced apart from one another. Each of the plurality of heating racks can have a plurality of parallel pipes, and a stand configured to secure the plurality of parallel pipes to a base of a biogas digester tank. A heating manifold can be configured to connect to the plurality of parallel pipes of each of the plurality of heating racks. The heating manifold may be configured to circulate a heat exchange fluid through the plurality of parallel pipes. The plurality of heating racks can be configured to be secured to the base of the biogas digester tank, and spaced a distance away from a vertical wall of the digester tank.

In yet another embodiment, a modular heating rack for a biogas digester tank is provided. The modular heating rack can include a plurality of parallel pipes arranged horizontally, and a stand configured to secure the plurality of parallel pipes to a base of the biogas digester tank. The plurality of parallel pipes may be connected to a heating manifold configured to circulate a heat exchange fluid through the plurality of parallel pipes. The heating rack may be a pre-assembled unit, and multiple heating racks can be connected in parallel to form a heating system for the biogas digester tank.

The modular heating rack for a biogas digester tank can include an inlet port and an outlet port that each terminate at an opposite end of the heating rack from the stand. The plurality of parallel pipes may be substantially straight, with a curvature of less than 20 degrees. The stand can include one or more apertures for allowing fluid to flow through the stand, and underneath the plurality of parallel pipes.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, process step, and structural changes may be made without departing from the scope of the disclosure. Accordingly, the scope of the disclosure is defined only by reference to the appended claims.

Figure 1:
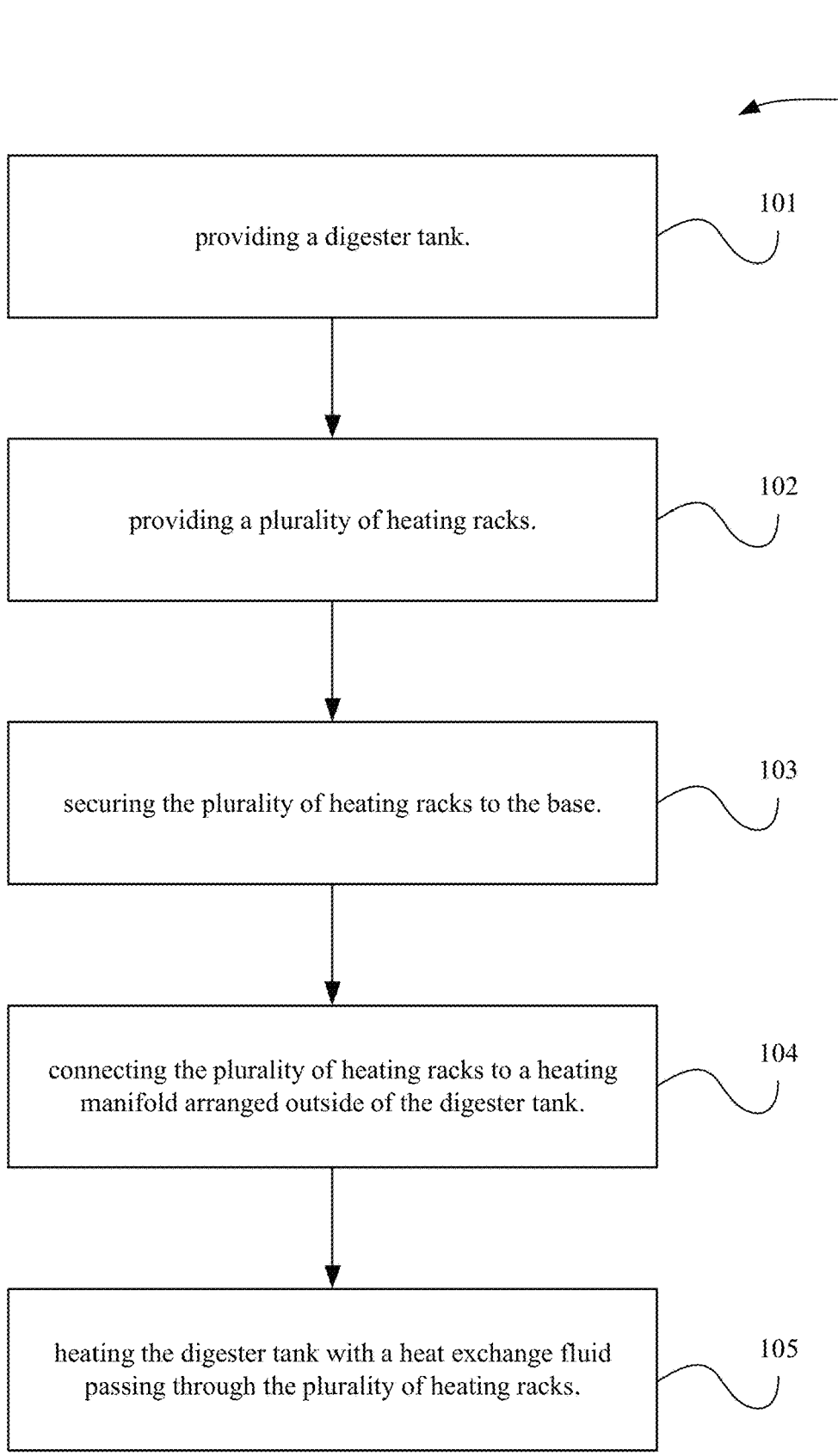
FIG. 1 is a flowchart of a method of manufacturing a biogas digester tank system according to an embodiment of the present disclosure.

As shown in FIG. 1, an embodiment of the present disclosure provides a method 100 of manufacturing a biogas digester tank system. The method may comprise the following steps.

At step 101, a digester tank is provided. The digester tank may comprise a base, a vertical wall surrounding the base, and a cover disposed on top of the vertical wall. The base may be concrete. The vertical wall may be concrete or metal. For example, the vertical wall may be stainless steel. The digester tank may have a curved shape. For example, the digester tank may be cylindrical or spherocylindrical.

At step 102, a plurality of heating racks are provided. The plurality of heating racks may each comprise a stand and a plurality of parallel pipes secured on top of the stand. Each heating rack may be a pre-assembled unit having varying heights and lengths, as suited for application in a particular digester tank. The dimensions of each heating rack may be advantageously limited to fit in a shipping container for ease of transport. According to embodiments of the present disclosure, the plurality of heating racks may be assembled in a factory as discrete units, and transported to the biogas generation system site for installation in the digester tank. Each heating rack may be tested and adjusted at the factory, for fast and simple installation in the digester tank.

The stand of each heating rack may comprise a plurality of stand assemblies. Each stand assembly may be a box steel structure. For example, each stand assembly may be comprised of lengths of box steel tubes that are joined together to form a rectangular structure. The plurality of stand assemblies may be spaced apart along the length of the heating rack. For example, there may be end stand assemblies arranged at each end of the heating rack, and there may be intermediate stand assemblies arranged between the end stand assemblies. The height of the stand may keep the plurality of parallel pipes a sufficient distance above the ground. For example, as methanation occurs in a biogas digester tank, sand and other sediments will fall to the ground, while gas rises to the top. Thus, it may be advantageous to keep the plurality of parallel pipes at the height of the decomposable substrate, above the sand and sediments, for efficient heat exchange.

The plurality of parallel pipes may be substantially linear. For example, each of the plurality of parallel pipes may have less than 20 degrees of curvature, less than 10 degrees of curvature, less than 5 degrees of curvature, or no curvature. The plurality of parallel pipes may be arranged horizontally. For example, the plurality of parallel pipes may be arranged horizontally in vertically-spaced rows. In an embodiment of the present disclosure, the plurality of parallel pipes may comprise two columns of vertically-spaced rows. The plurality of parallel pipes may be stainless steel pipes. Each of the plurality of parallel pipes may have uniform lengths and diameters. Lengths of the plurality of parallel pipes may be comprised of single pipes or multiple pipes connected end-to-end. Each pipe connected end-to-end may by connected by a coupling. For example, the coupling may be a Victaulic coupling. Alternatively, each pipe connected end-to-end may be connected by welds. It can be appreciated that welds would be difficult to use in prior art heating systems, as welding is difficult to be performed at the installation site. Instead, welding is easily performed at the factory when manufacturing the plurality of heating racks of the present disclosure. When couplings or welds are used, pipe connections can be tested at the factory, which further saves installation time.

The plurality of parallel pipes in each heating rack may be connected to one another to form a flow path. For example, ends of the plurality of parallel pipes may be received by end members of the heating rack. The end members may redirect flow from one of the parallel pipes to the next in the flow path. The flow path may begin at an inlet pipe and end at an outlet pipe. The inlet pipe and the outlet pipe may terminate at the top of the heating rack, emanating in a vertical direction. The flow path may be designed using the Tichelmann System for uniform heat distribution and low pressure losses. Accordingly, each of the plurality of heating racks may operate in parallel, each with their own flow path. Such design offers modularity in comparison to prior art heating systems, which operate in series and have a single flow path for the entire heating system. Particular advantages of such modularity include the ability to quickly identify defects in the heating system, and the ability to plug-and-play new/additional heating racks when necessary.

The plurality of parallel pipes may be secured to the stand. Where the stand comprises a plurality of stand assemblies, the plurality of parallel pipes may be secured to each of the plurality of stand assemblies. For example, the end members may be directly secured to the end stand assemblies. The plurality of parallel pipes may be secured to the intermediate stand assemblies by vertical rods that individually secure to each of the vertically-spaced parallel pipes and to the intermediate stand assemblies.

At step 103, the plurality of heating racks are secured to the base. For example, the stand of each heating rack may be secured to the base. Each stand may be secured to the base via anchor bolts. Each stand may be secured to the base adjacent to the vertical wall. For example, the stand may be secured to the base at an average distance 1700 mm from the vertical wall. Other distances, closer to and farther from the vertical wall are possible. In some embodiments, where each stand comprises a plurality of stand assemblies, each of the plurality of stand assemblies may be separately secured to the base.

In an embodiment of the present disclosure, the plurality of heating racks may be arranged in a polygon shape about the inner circumference of the digester tank. For example, there may be six heating racks arranged in a hexagon shape about the inner circumference of the digester tank. The plurality of heating racks may be spaced apart from one another. For example, adjacent heating racks may be spaced apart by 2500 mm between them. In an embodiment of the present disclosure, the digester tank may include agitators. The agitators may be mounted to the base, located off-center, and configured to move the substrate around the digester tank. In addition, agitators may be mounted to the vertical walls, located between adjacent heating racks. The wall-mounted agitators may be movable up and down the vertical walls, and may be adjustable to be angled left or right. For example, the wall-mounted agitators may be adjustable up to 180 degrees. By angling the wall mounted agitators, substrate can be directed to move toward and/or through one of the heating racks for improved heat transfer. It can be appreciated that prior art heating systems directly mounted to the walls of the digester tank or mounted to the base near the wall could not accommodate the wall-mounted agitators of the present disclosure.

Adjacent heating racks of the plurality of heating racks may be connected to each other. For example, adjacent heating racks may be connected to each other by stainless steel rods bolted at each end. By connecting adjacent heating racks, their stability is improved. In some embodiments of the present disclosure, where the digester tank includes wall-mounted agitators, adjacent heating racks may be connected to each other where there is not a wall-mounted agitator between them.

At step 104, the plurality of heating racks are connected to a heating manifold. The heating manifold may be arranged outside of the digester tank. In some embodiments, the digester tank may have an inlet port and an outlet port. The plurality of parallel pipes may be connected to the heating manifold via the inlet port and the outlet port. For example, the inlet pipe may be connected to the inlet port and the outlet pipe may be connected to the outlet port. The digester tank may have a plurality of inlet ports and outlet ports. Pairs of adjacent heating racks may be connected to the same inlet port and outlet port. The inlet port and the outlet port may be positioned at the same height above the height of the heating rack for proper venting of trapped air in the plurality of parallel pipes.

At step 105, the digester tank can be heated with a heat exchange fluid passing through the plurality of heating racks. In one example, the heating manifold may be configured to circulate a heat exchange fluid through the plurality of parallel pipes of each heating rack. Specifically, the heating manifold may be configured to circulate a heat exchange fluid through the flow path of the plurality of parallel pipes. The heat exchange fluid may be water.

With the method 100 of manufacturing a biogas digester tank system of the present disclosure, a digester tank system with a heating system is provided that is easy to install and maintain, and is suitable for digester tanks of varying sizes and materials. Specifically, the plurality of heating racks provide a modular heating system for the digester tank system that are easy to install due to their simple connection to the digester tank, easy to maintain due to their pre-assembly and prior testing, and suitable for varying digester tanks due to the modularity of providing heating racks of various sizes as pre-assembled units.

As shown in FIGS. 2-6, another embodiment of the present disclosure provides a biogas digester tank system 200. The biogas digester tank system 200 may comprise a digester tank 210. The digester tank 210 may comprise a base 212 and a vertical wall 214 surrounding the base 212. The base 212 may be circular, having a diameter of between 25 m and 35 m. For example, the base 212 may have a diameter of about 35 m. The vertical wall 214 may have a height of about 7.5 m. The vertical wall 214 may have other heights, for example, 9 m. The digester tank 210 may further comprise a cover 216 disposed on top of the vertical wall 214. The digester tank 210 may be about 14 m tall with the cover 216. The base 212 may be concrete. The vertical wall 214 may be concrete or metal. For example, the vertical wall 214 may be stainless steel. The digester tank 210 may have a curved shape. For example, the digester tank 210 may be cylindrical or spherocylindrical.

As shown in FIGS. 2-10, the biogas digester tank system 200 may further comprise a heating system 300. The heating system 300 may comprise a plurality of heating racks 301. The plurality of heating racks 301 may each comprise a stand 310 and a plurality of parallel pipes 320 secured on top of the stand 310. Each heating rack 301 may be a pre-assembled unit having varying heights and lengths, as suited for application in a particular digester tank 210. For example, each heating rack 301 may be about 3.4 m high and 11.7 m long. The dimensions of each heating rack 301 may be advantageously limited to fit in a shipping container for ease of transport. According to embodiments of the present disclosure, the plurality of heating racks 301 may be assembled in a factory as discrete units, and transported to the biogas generation system site for installation in the digester tank 210. Each heating rack 301 may be tested and adjusted at the factory, for fast and simple installation in the digester tank 210.

As shown in FIGS. 7-10, the stand 310 of each heating rack 301 may comprise a plurality of stand assemblies 311. Each stand assembly 311 may be a box steel structure. For example, each stand assembly 311 may be comprised of lengths of box steel tubes that are joined together to form a rectangular structure. The plurality of stand assemblies 311 may be spaced apart along the length of the heating rack 301. For example, there may be end stand assemblies 311a arranged at each end of the heating rack 301, and there may be intermediate stand assemblies 311b arranged between the end stand assemblies 311a. The stand 310 may be about 1.2 m high. The height of the stand 310 may keep the plurality of parallel pipes 320 a sufficient distance above the base 212 of the digester tank 210. For example, as methanation occurs in a biogas digester tank 210, sand and other sediments will fall to the ground, while gas rises to the top. Thus, it may be advantageous to keep the plurality of parallel pipes 320 at the height of the decomposable substrate, above the sand and sediments, for efficient heat exchange. Moreover, the stand 310 may be configured to have one or more apertures (e.g. central opening 310a) for allowing material in the biogas digester tank to flow through the stand 310.

The plurality of parallel pipes 320 may be substantially linear. For example, each of the plurality of parallel pipes 320 may have less than 20 degrees of curvature, less than 10 degrees of curvature, or less than 5 degrees of curvature. The plurality of parallel pipes 320 may be arranged horizontally. For example, the plurality of parallel pipes 320 may be arranged horizontally in vertically-spaced rows. In an embodiment of the present disclosure, the plurality of parallel pipes 320 may comprise two columns of vertically-spaced rows. The plurality of parallel pipes 320 may be stainless steel pipes. Each of the plurality of parallel pipes 320 may have uniform lengths and diameters. For example, each of the plurality of parallel pipes 320 may have a length between 5 m and 12 m, and a diameter between 60 mm and 80 mm. Lengths of the plurality of parallel pipes 320 may be comprised of single pipes or multiple pipes connected end-to-end. Each pipe connected end-to-end may by connected by a coupling (rather than welding). For example, the coupling may be a Victaulic coupling. Alternatively, each pipe may be connected end-to-end may be connected by welds. It can be appreciated that welds would be difficult to use in prior art heating systems, as welding is difficult to be performed at the installation site. Instead, welding is easily performed at the factory when manufacturing the plurality of heating racks 301 of the present disclosure. When couplings or welds are used, pipe connections can be tested at the factory, which further saves installation time.

The plurality of parallel pipes 320 in each heating rack 301 may be connected to one another to form a flow path. For example, ends of the plurality of parallel pipes 320 may be received by end members 321 of the heating rack 301. The end members 321 may redirect flow from one of the parallel pipes 320 to the next in the flow path. The flow path may begin at an inlet pipe 323 and end at an outlet pipe 324. The inlet pipe 323 and the outlet pipe 324 may terminate at the top of the heating rack 301, emanating in a vertical direction. The flow path may be designed using the Tichelmann System for uniform heat distribution and low pressure losses. Accordingly, each of the plurality of heating racks 301 may operate in parallel, each with their own flow path. Such design offers modularity in comparison to prior art heating systems, which operate in series and have a single flow path for the entire heating system. Particular advantages of such modularity include the ability to quickly identify defects in the heating system 300, improved thermal properties, as well as the ability to plug-and-play new/additional heating racks when necessary.

The plurality of parallel pipes 320 may be secured to the stand 310. Where the stand 310 comprises a plurality of stand assemblies 311, the plurality of parallel pipes 320 may be secured to each of the plurality of stand assemblies 311. For example, the end members 321 may be directly secured to the end stand assemblies 311a. The plurality of parallel pipes 320 may be secured to the intermediate stand assemblies 311b by vertical rods 312 that individually secure to each of the vertically-spaced parallel pipes 320 and to the intermediate stand assemblies 311b.

As shown in FIGS. 3-6, the plurality of heating racks 301 may be secured to the base 212 of the digester tank 210. For example, the stand 310 of each heating rack 301 may be secured to the base 212. Each stand 310 may be secured to the base 212 via anchor bolts. Each stand 310 may be secured to the base 212 adjacent to the vertical wall 214. For example, the stand 310 may be secured to the base 212 at an average distance of 100 mm to 2000 mm from the vertical wall 214. In some embodiments, where each stand 310 comprises a plurality of stand assemblies 311, each of the plurality of stand assemblies 311 may be separately secured to the base 212.

Figure 2:
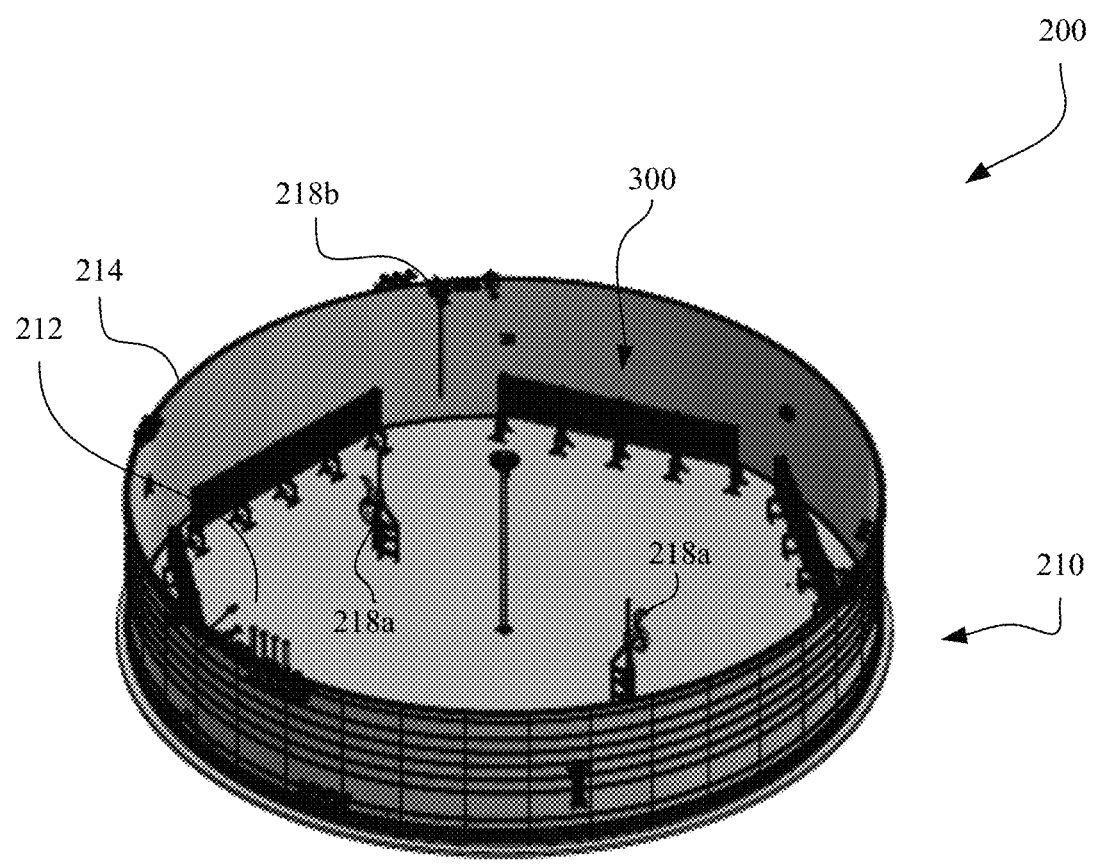
FIG. 2 is a perspective view of a biogas digester tank system according to an embodiment of the present disclosure.
Figure 3:
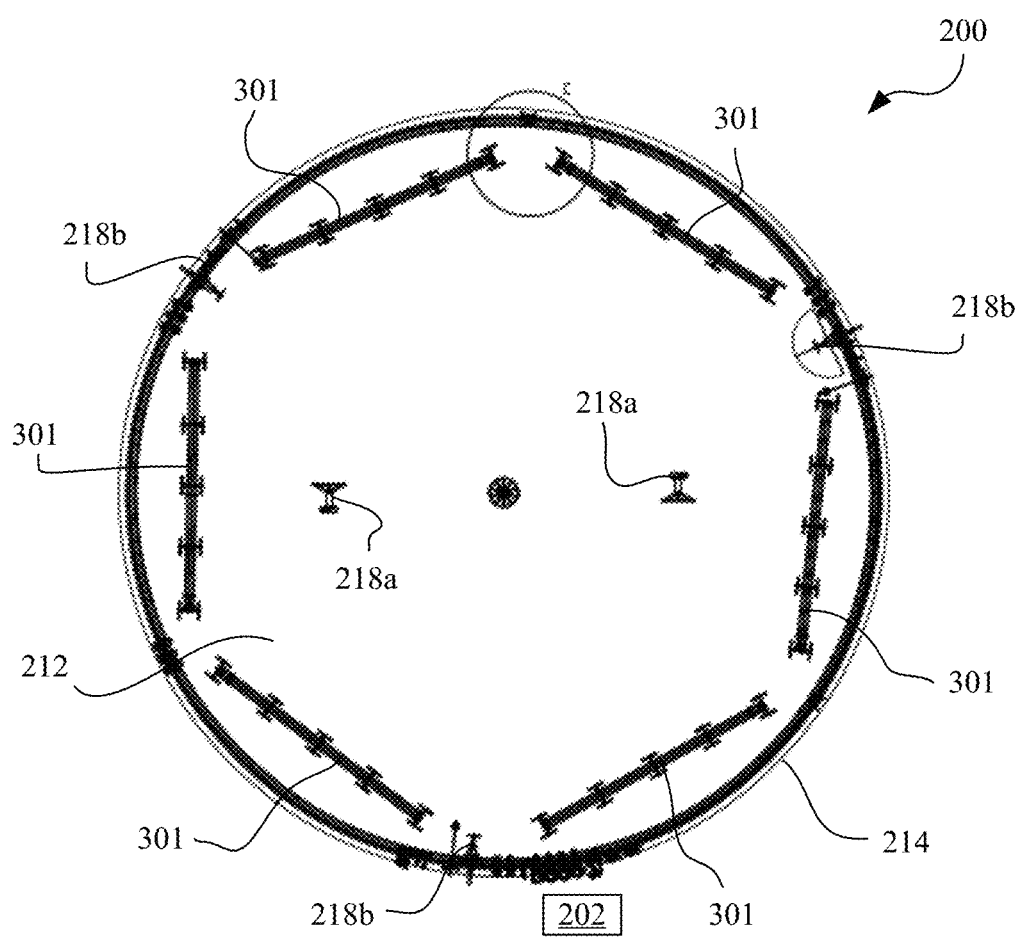
FIG. 3 is a top view thereof.

In an embodiment of the present disclosure, the plurality of heating racks 301 may be arranged in a polygon shape about the inner circumference of the digester tank 210. For example, as shown in FIGS. 2-3, there may be six heating racks 301 arranged in a hexagon shape about the inner circumference of the digester tank 210. The plurality of heating racks 301 may be spaced apart from one another. For example, adjacent heating racks 301 may have 1.5 m to 3 m between them.

As shown in FIGS. 3-6, the biogas digester tank 210 may include agitators 218a, 218b. Agitators 218a may be mounted to the base 212, located off-center, and configured to move the substrate around the digester tank 210. In addition, agitators 218b may be mounted to the vertical walls 214, located between adjacent heating racks 301. The wall-mounted agitators 218b may be movable up and down the vertical walls 214, and may be adjustable to be angled left or right. For example, the wall-mounted agitators 218b may be adjustable up −90 to 90 degrees. By angling the wall mounted agitators 218b, substrate can be directed to move toward and/or through one of the heating racks 301 for improved heat transfer. It can be appreciated that prior art heating systems directly mounted to the walls of the digester tank or mounted to the base near the wall could not accommodate the wall-mounted agitators 218b of the present disclosure.

Adjacent heating racks of the plurality of heating racks 301 may be connected to each other. For example, adjacent heating racks 301 may be connected to each other by stainless steel rods bolted at each end. By connecting adjacent heating racks 301, their stability is improved. In some embodiments of the present disclosure, where the digester tank 210 includes wall-mounted agitators 218b, adjacent heating racks 301 may be connected to each other where there is not a wall-mounted agitator 218b between them.

Figure 4:
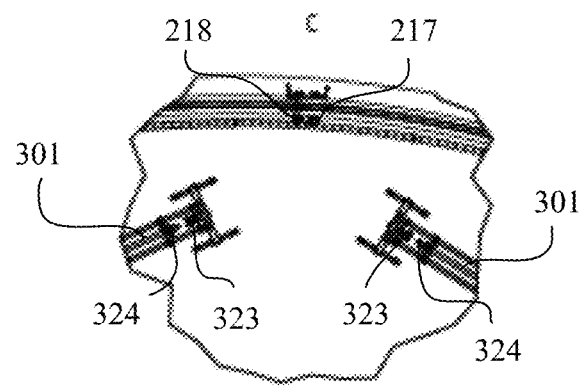
FIG. 4 is a detail view of portion C of FIG. 3.
Figure 5:
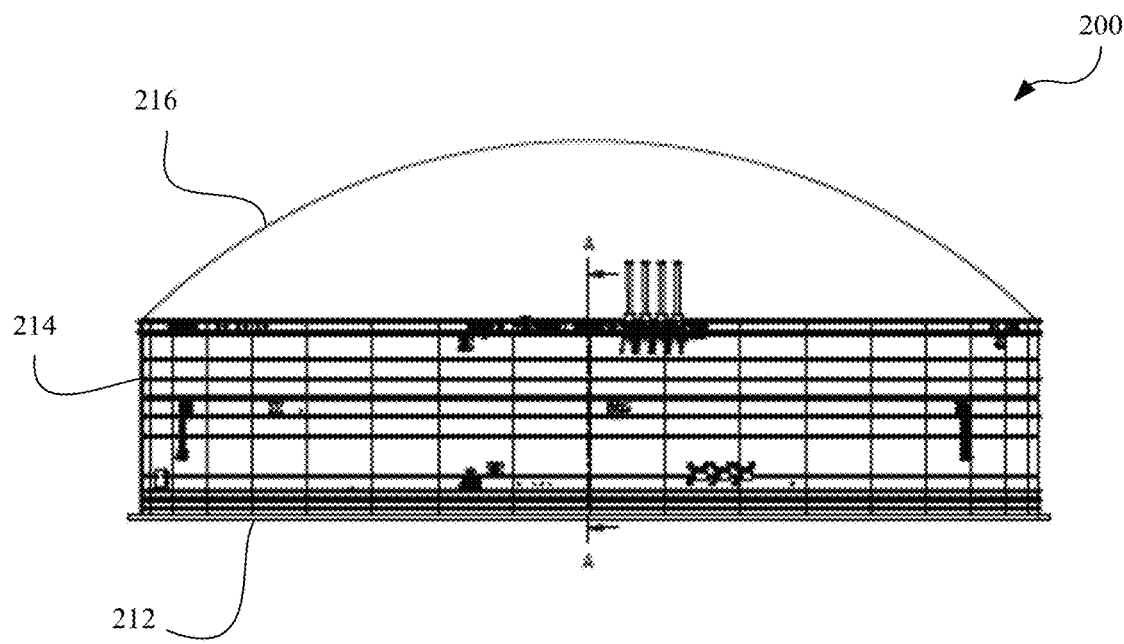
FIG. 5 is a side view of a biogas digester tank system according to an embodiment of the present disclosure.
Figure 6:
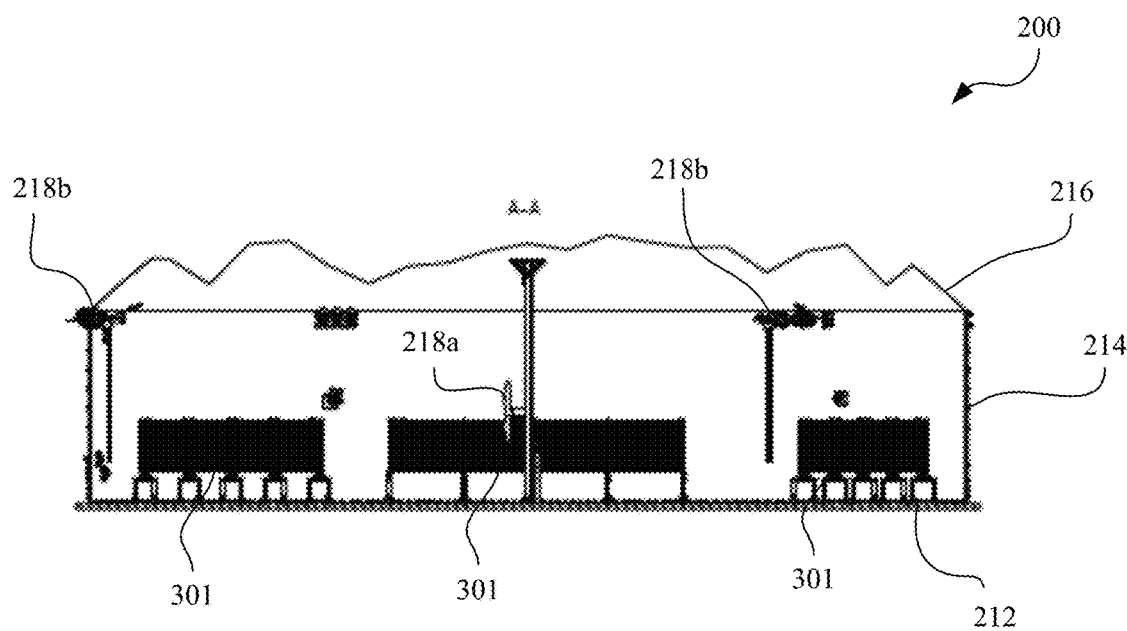
FIG. 6 is a section view taken along line A-A of FIG. 5.
Figure 7:
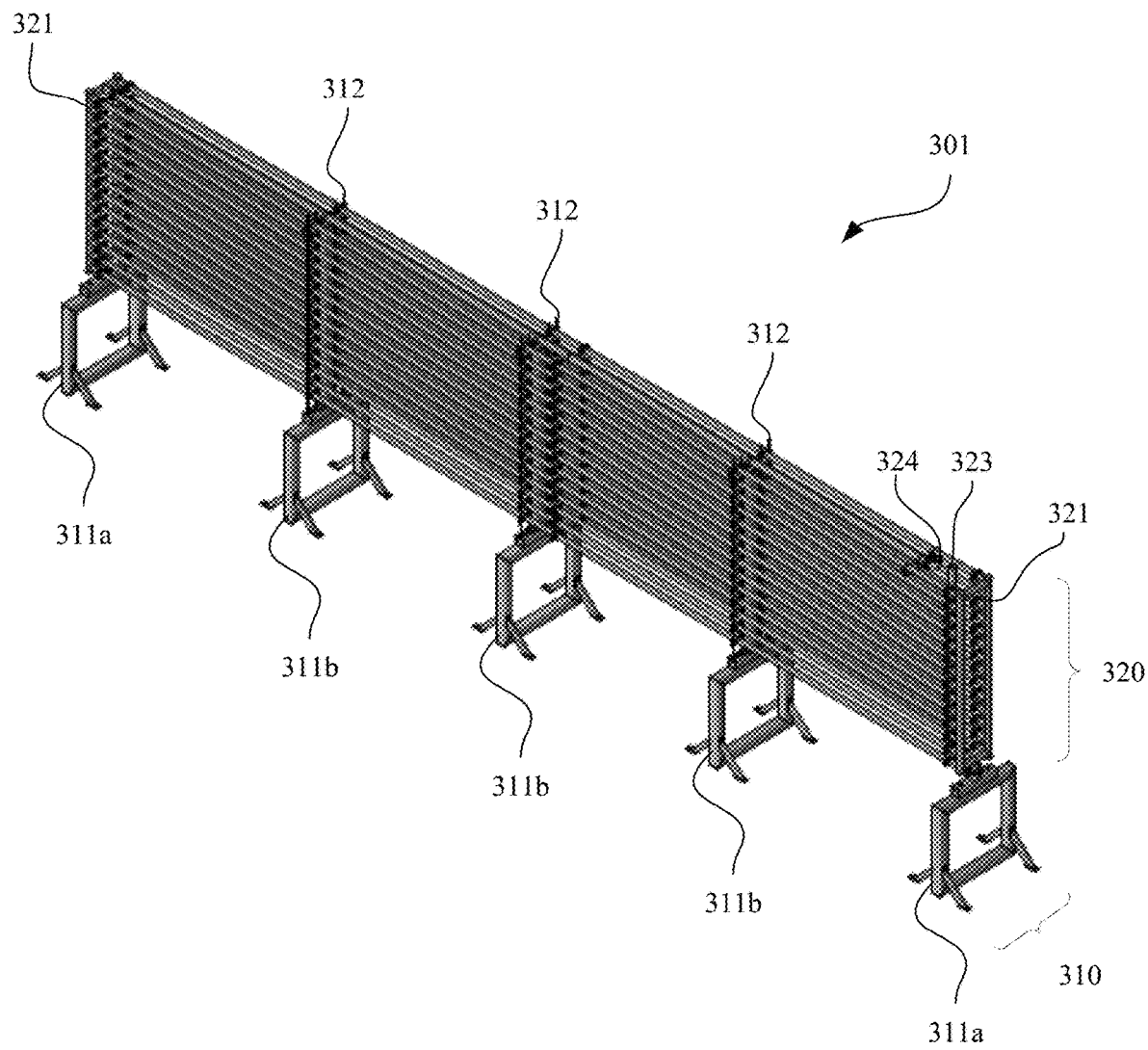
FIG. 7 is a perspective view of a heating system for a biogas digester tank according to an embodiment of the present disclosure.
Figure 8:
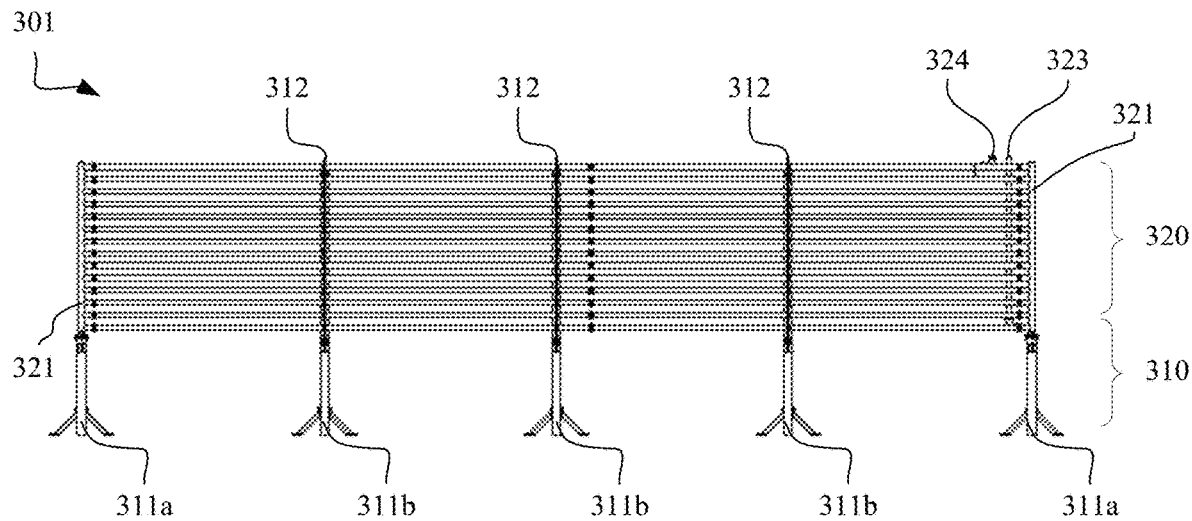
FIG. 8 is a side view thereof.
Figure 9:
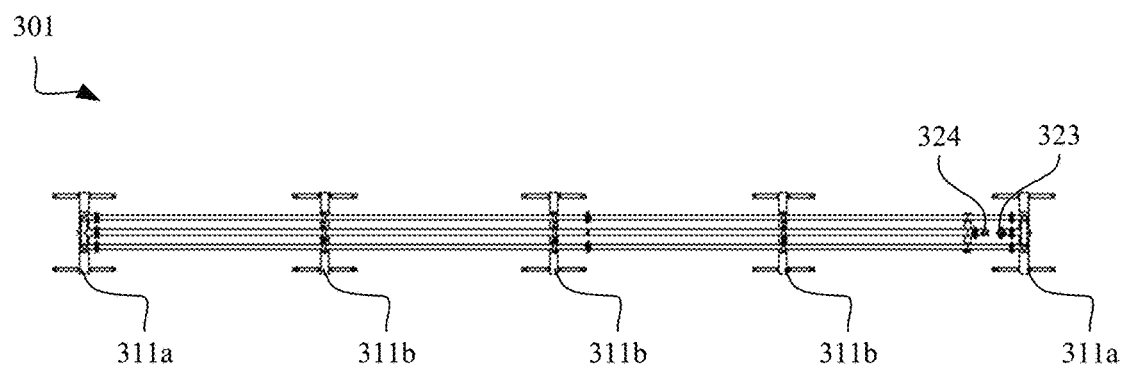
FIG. 9 is a top view thereof.
Figure 10:
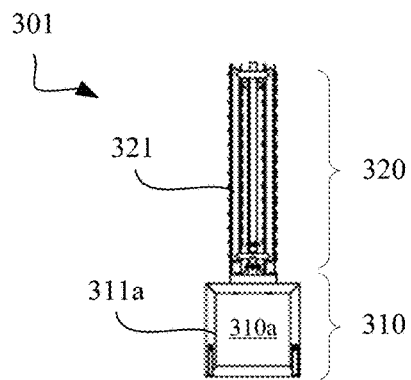
FIG. 10 is a front view thereof.

The biogas digester tank system 200 may further comprise a heating manifold 202. The heating manifold may be arranged outside of the digester tank 210. As shown in FIG. 4, the digester tank 210 may have an inlet port 217 and an outlet port 218. The plurality of parallel pipes 320 may be connected to the heating manifold via the inlet port 217 and the outlet port 218. For example, the inlet pipe 323 may be connected to the inlet port 217 and the outlet pipe 324 may be connected to the outlet port 218. The digester tank 210 may have a plurality of inlet ports 217 and outlet ports 218. Pairs of adjacent heating racks 301 may be connected to the same inlet port 217 and outlet port 218. The inlet port 217 and the outlet port 218 may be positioned at the same height above the height of the heating rack 301 for proper venting of trapped air in the plurality of parallel pipes 320. For example, the inlet port 217 and the outlet port 218 may be position about 4 m above the base 212. The heating manifold may be configured to circulate a heat exchange fluid through the plurality of parallel pipes 320 of each heating rack 301.

For example, the heating manifold may be configured to circulate a heat exchange fluid through the flow path of the plurality of parallel pipes 320. The heat exchange fluid may be water.

Figure 11:
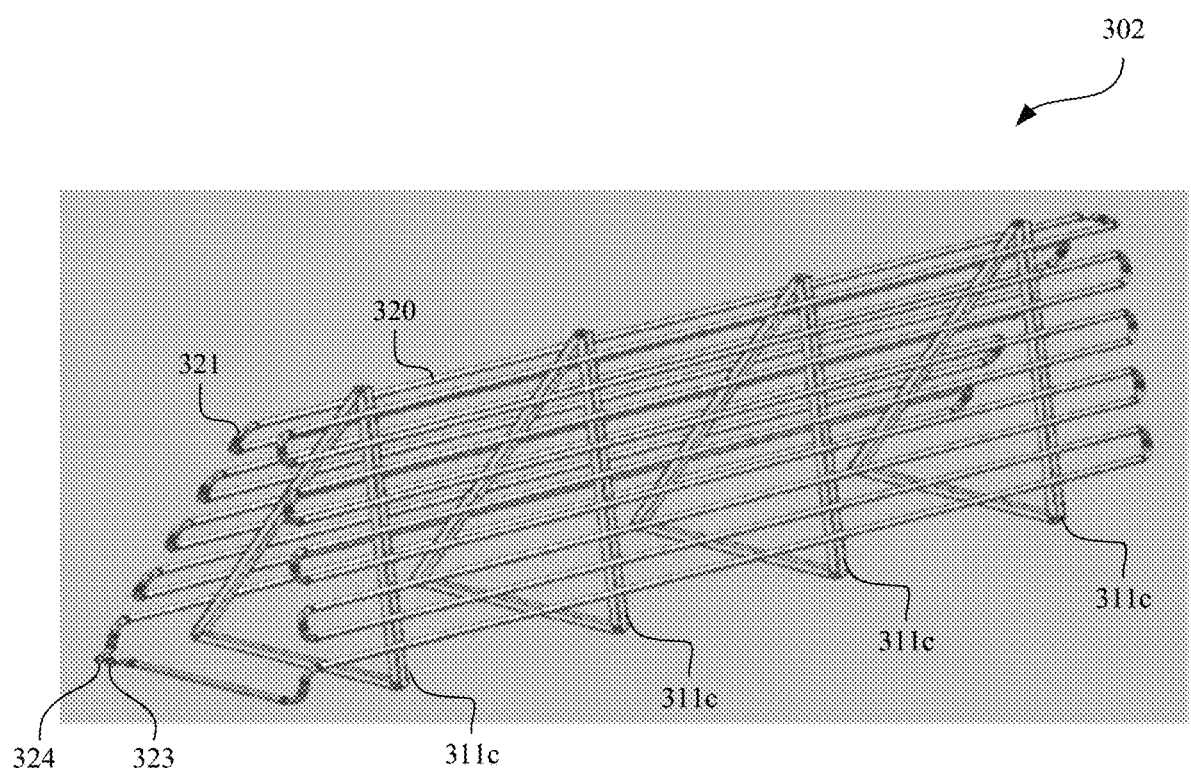
FIG. 11 is a perspective view of a heating system for a biogas digester tank according to another embodiment of the present disclosure.

According to an embodiment of the present disclosure, as shown in FIG. 11, the heating system 300 may comprise a plurality of heating racks 302. The plurality of heating racks 302 may differ from the plurality of heating racks 301 in that the plurality of stand assemblies 311 may comprise triangular stand assemblies 311c. In this configuration, a horizontal base portion of each triangular stand assembly 311c may be secured to the base 212, and the plurality of parallel pipes 320 may be secured to vertically-angled side portions of each triangular stand assembly 311c. Ends of the plurality of parallel pipes 320 may be received by end members 321 of the heating rack 302. The end members 321 may redirect flow from one of the parallel pipes 320 to the next in the flow path. The inlet pipe 323 and the outlet pipe 324 may terminate at the bottom of the heating rack 302, emanating in a horizontal direction.

With the biogas digester tank system 200 of the present disclosure, the heating system 300 is easy to install and maintain, and is suitable for digester tanks 210 of varying sizes and materials. Specifically, the heating racks provide a modular heating system for the digester tank system 200 that is easy to install due to their simple connection to the digester tank 210, easy to maintain due to their pre-assembly and prior testing, and suitable for varying digester tanks 210 due to the modularity of providing heating racks of various sizes as pre-assembled units.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. A biogas digester tank heating system, comprising:
a plurality of heating racks configured to be spaced apart from one another, each of the plurality of heating racks comprising:
a plurality of parallel pipes; and
a stand configured to secure the plurality of parallel pipes to a base of a biogas digester tank;
a heating manifold configured to connect to the plurality of parallel pipes of each of the plurality of heating racks, wherein the heating manifold is configured to circulate a heat exchange fluid through the plurality of parallel pipes; and
an agitator mounted to a vertical wall of the biogas digester tank;
wherein the plurality of heating racks are configured to be secured to the base of the biogas digester tank in a circumferential arrangement spaced at regular intervals within the biogas digester tank, and spaced a distance away from the vertical wall of the biogas digester tank, and the agitator mounted to the vertical wall of the biogas digester tank is disposed in a space between adjacent heating racks of the plurality of heating racks and between the plurality of heating racks and the vertical wall.

2. The biogas digester tank heating system of claim 1, further comprising an agitator mounted to the base of the biogas digester tank and located off-center in a space surrounded by the plurality of heating racks.

3. The biogas digester tank heating system of claim 1, wherein the agitator mounted to the vertical wall of the biogas digester tank is vertically movable relative to the vertical wall and angularly adjustable toward each of the adjacent heating racks.

4. The biogas digester tank heating system of claim 1, wherein the plurality of parallel pipes are substantially straight, with a curvature of less than 20 degrees.

5. The biogas digester tank system of claim 1, wherein the plurality of heating racks are secured to the base spaced apart from one another, with a minimum distance between ends of adjacent heating racks of 0.1 m.

6. The biogas digester tank heating system of claim 1, wherein an inlet pipe of the plurality of parallel pipes of each heating rack is connected to an inlet port in the biogas digester tank, and an outlet pipe of the plurality of parallel pipes of each heating rack is connected to an outlet port in the biogas digester tank.

7. The biogas digester tank heating system of claim 6, wherein the inlet pipe and the outlet pipe emanate vertically from each heating rack, and the inlet port and the outlet port are located at a height above the height of the heating rack.

8. The biogas digester tank heating system of claim 6, wherein the biogas digester tank comprises a plurality of inlet ports and a plurality of outlet ports, and each of the plurality of inlet ports and each of the plurality of outlet ports is connected to at least one of the plurality of heating racks.

9. The biogas digester tank heating system of claim 8, wherein each pair of adjacent heating racks is connected to one of the plurality of inlet ports and one of the plurality of outlet ports.

10. The biogas digester tank heating system of claim 8, wherein each of the plurality of inlet ports and each of the plurality of outlet ports are disposed in a space between adjacent heating racks of the plurality of heating racks.

* * * * *